United States Patent

Sakaue et al.

(10) Patent No.: US 8,664,404 B2
(45) Date of Patent: Mar. 4, 2014

(54) METHOD FOR PRODUCING 3-HALO-1,2-BENZISOTHIAZOLES

(75) Inventors: Shigeki Sakaue, Kako-gun (JP); Sachio Iida, Kako-gun (JP)

(73) Assignee: Sumitomo Seika Chemicals Co., Ltd., Kako-gun (JP)

( * ) Notice: Subject to any disclaimer, the term of this patent is extended or adjusted under 35 U.S.C. 154(b) by 0 days.

(21) Appl. No.: 13/634,450

(22) PCT Filed: Mar. 14, 2011

(86) PCT No.: PCT/JP2011/055943
§ 371 (c)(1),
(2), (4) Date: Sep. 12, 2012

(87) PCT Pub. No.: WO2011/125423
PCT Pub. Date: Oct. 13, 2011

(65) Prior Publication Data
US 2013/0005983 A1   Jan. 3, 2013

(30) Foreign Application Priority Data
Apr. 2, 2010 (JP) ................. 2010-086377

(51) Int. Cl.
C07D 275/04 (2006.01)
(52) U.S. Cl.
USPC ....................................... 548/207
(58) Field of Classification Search
None
See application file for complete search history.

(56) References Cited

U.S. PATENT DOCUMENTS

| | | | |
|---|---|---|---|
| 4,147,698 A | 4/1979 | Wade et al. | |
| 4,148,798 A | 4/1979 | Wade et al. | |
| 4,590,196 A | 5/1986 | Smith et al. | |
| 5,856,504 A * | 1/1999 | Kagano et al. | 548/207 |
| 5,883,258 A | 3/1999 | Kraus et al. | |
| 2006/0252785 A1 | 11/2006 | Blake et al. | |
| 2009/0069317 A1 | 3/2009 | Pohlman et al. | |

FOREIGN PATENT DOCUMENTS

| | | |
|---|---|---|
| EP | 0 846 692 A1 | 6/1998 |
| JP | 54-106464 A | 8/1979 |
| JP | 61-112063 A | 5/1986 |
| JP | 63-83085 A | 4/1988 |
| JP | 10-168070 A | 6/1998 |
| JP | 11-199540 A | 7/1999 |
| JP | 2008-540370 A | 11/2008 |
| JP | 2009-516667 A | 4/2009 |
| WO | WO 2006/091858 A1 | 8/2006 |
| WO | WO 2007/057407 A2 | 5/2007 |

OTHER PUBLICATIONS

International Search Report issued Apr. 5, 2011 in PCT/JP2011/055943.
Extended European Search Report Issued Jul. 30, 2013 in Patent Application No. 11765325.3.

* cited by examiner

*Primary Examiner* — Wu-Cheng Winston Shen
*Assistant Examiner* — Ana Z Muresan
(74) *Attorney, Agent, or Firm* — Oblon, Spivak, McClelland, Maier & Neustadt, L.L.P.

(57) ABSTRACT

A method for producing a 3-halo-1,2-benzisothiazole represented by the general formula (2):

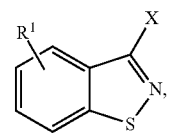

(2)

wherein $R^1$ is a hydrogen atom, an alkyl group having 1 to 4 carbon atoms, an alkoxy group having 1 to 4 carbon atoms, an alkoxycarbonyl group having 2 to 5 carbon atoms, a nitro group or a halogen atom, and X is a halogen atom, the method characterized by reacting a 1,2-benzisothiazol-3-one represented by the general formula (1):

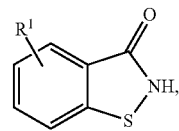

(1)

wherein $R^1$ is the same group as the $R^1$ defined in the above general formula (2), with a thionyl halide in a polar solvent. The 3-halo-1,2-benzisothiazole obtainable according to the method of the present invention is suitably used as production raw materials and the like for a medicament and the like.

14 Claims, No Drawings

METHOD FOR PRODUCING 3-HALO-1,2-BENZISOTHIAZOLES

TECHNICAL FIELD

The present invention relates to a method for producing a 3-halo-1,2-benzisothiazole. More specifically, the present invention relates to a method for producing a 3-halo-1,2-benzisothiazole which is useful as production raw materials for a medicament and the like.

BACKGROUND ART

Conventionally, as methods for producing a 3-halo-1,2-benzisothiazole, (A) a method including reacting 1,2-benzisothiazole and phosphorus oxychloride or phosphorus trichloride in the absence of a solvent, to give 3-chloro-1,2-benzisothiazole (see, Patent Publication 1):

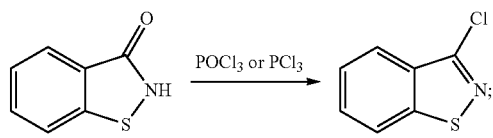

(B) a method including reacting 1,2-benzisothiazole and phosgene in the presence of a catalyst such as dibutylformamide, to give 3-chloro-1,2-benzisothiazole (see, Patent Publication 2):

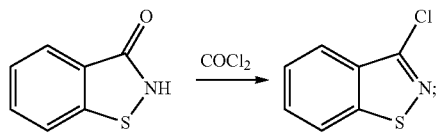

(C) a method including reacting thionyl chloride and methylamine with dithiosalicylic acid to produce an amide form, and subsequently reacting the amide form with phosphorus tetrachloride, to give 3-chloro-1,2-benzisothiazole (see, Patent Publication 3):

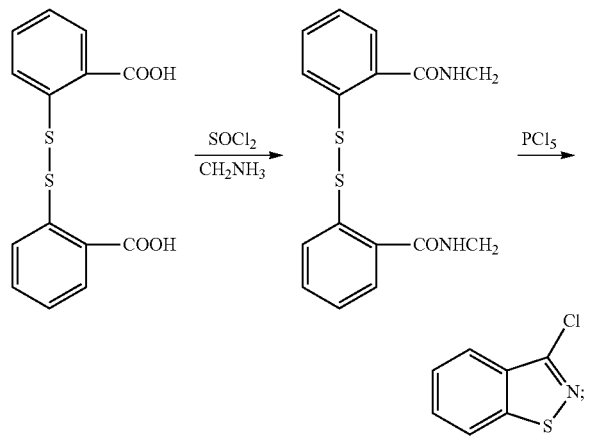

and the like have been known.

However, the method (A) has some disadvantages that separation of a phosphorus halide which is a side reaction product is difficult, thereby necessitating the use of a phosphorus oxychloride or a phosphorus trichloride which has some disadvantages in wastewater treatment, and that the yield is also low. The method (B) has some disadvantages that phosgene which is very highly toxic and has some disadvantages in handling safely, so that the method can hardly be said to be an industrially advantageous method. The method (C) has some disadvantages that expensive dithiosalicylic acid is used, that a large number of reaction steps need to be taken, and that the yield is also low, so that the method can hardly be said to be an industrially advantageous method.

PRIOR ART PUBLICATIONS

Patent Publications

Patent Publication 1: Japanese Patent Laid-Open No. Sho-61-112063 (claim 30, page 15 (Example 19))
Patent Publication 2: Japanese Patent Laid-Open No. Hei-10-168070 (claim 7)
Patent Publication 3: Japanese Patent Laid-Open No. Sho-63-83085 (page 8 (Reference Example 4))

SUMMARY OF THE INVENTION

Problems To Be Solved By The Invention

An object of the present invention is to provide a method for industrially advantageously producing a 3-halo-1,2-benzisothiazole without using an expensive raw material.

Means To Solve The Problems

In other words, the gist of the present invention relates to a method for producing a 3-halo-1,2-benzisothiazole represented by the general formula (2):

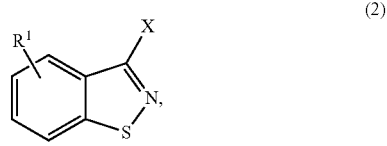

(2)

wherein $R^1$ is a hydrogen atom, an alkyl group having 1 to 4 carbon atoms, an alkoxy group having 1 to 4 carbon atoms, an alkoxycarbonyl group having 2 to 5 carbon atoms, a nitro group or a halogen atom, and X is a halogen atom, the method characterized by reacting a 1,2-benzisothiazol-3-one represented by the general formula (1):

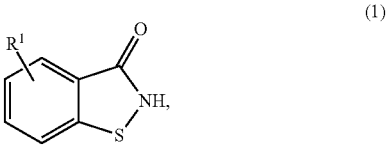

(1)

wherein $R^1$ is the same group as the $R^1$ defined in the above general formula (2),
with a thionyl halide in a polar solvent.

Effects of the Invention

According to the present invention, a 3-halo-1,2-benzisothiazole which is useful as production raw materials for a medicament or the like can be industrially advantageously produced without using an expensive raw material.

Modes For Carrying Out The Invention

The 1,2-benzisothiazol-3-one usable in the present invention is a compound represented by the above general formula (1).

In the above general formula (1), $R^1$ is a hydrogen atom, an alkyl group having 1 to 4 carbon atoms, an alkoxy group having 1 to 4 carbon atoms, an alkoxycarbonyl group having 2 to 5 carbon atoms, a nitro group or a halogen atom.

The alkyl group having 1 to 4 carbon atoms includes a methyl group, an ethyl group, an n-propyl group, an isopropyl group, an n-butyl group, an isobutyl group, a sec-butyl group, a tert-butyl group and the like.

The alkoxy group having 1 to 4 carbon atoms includes a methoxy group, an ethoxy group, a propoxy group, a butoxy group and the like.

The alkoxycarbonyl group having 2 to 5 carbon atoms includes a methoxycarbonyl group, an ethoxycarbonyl group, a propoxycarbonyl group, a butoxycarbonyl group and the like.

The halogen atom includes a fluorine atom, a chlorine atom, a bromine atom and the like.

Specific examples of the 1,2-benzisothiazol-3-ones represented by the above general formula (1) include 1,2-benzisothiazol-3-one, 7-methyl-1,2-benzisothiazol-3-one, 5-butyl-1,2-benzisothiazol-3-one, 6-methoxy-1,2-benzisothiazol-3-one, 6-methoxycarbonyl-1,2-benzisothiazol-3-one, 7-nitro-1,2-benzisothiazol-3-one, 6-chloro-1,2-benzisothiazol-3-one and the like.

The 1,2-benzisothiazol-3-one can be produced by known methods. For example, the 1,2-benzisothiazol-3-one can be produced by reacting a 2-halobenzonitrile with an alkanethiol in a heterogenous system in the presence of a base to give a 2-(alkylthio)benzonitrile, and further reacting a reaction mixture with a halogenating agent such as chlorine or sulfuryl chloride in the presence of water.

The thionyl halide usable in the present invention includes thionyl chloride, thionyl bromide and the like. Among them, the thionyl chloride is preferably used from the viewpoint of economical advantages and availability.

The thionyl halide is used in an amount of preferably from 0.8 to 5 mol, and more preferably from 1 to 3 mol based on 1 mol of 1,2-benzisothiazol-3-one, from the viewpoint of reducing the amount of 1,2-benzisothiazol-3-one remaining unreacted and from the viewpoint of obtaining appropriate effects matching the amount used.

The polar solvent usable in the present invention includes N,N-dimethylformamide, N,N-diethylformamide, N,N-dibutylformamide, sulfolane, pyridine and the like. Among them, the N,N-dimethylformamide is preferably used from the viewpoint of economical advantages and availability.

The polar solvent is used in an amount of preferably from 1 to 6 mol, more preferably from 1.5 to 5.5 mol, and especially preferably from 2.2 to 5 mol based on 1 mol of 1,2-benzisothiazol-3-one, from the viewpoint of smoothly progressing the reaction and from the viewpoint of obtaining appropriate effects matching the amount used.

In the present invention, in addition to the above polar solvent, a solvent which is inert to the reaction can be mixed and used. The solvent which is inert to the reaction includes hydrocarbons such as n-hexane, cyclohexane and n-heptane; halogenated hydrocarbons such as dichloroethane, dichloromethane and chloroform; aromatic hydrocarbons such as benzene, toluene, xylene, chlorobenzene, dichlorobenzene and trichlorobenzene. Among them, toluene, chlorobenzene or the like is preferably used. It is preferable that the solvent which is inert to the reaction is used in an amount of usually from 50 to 2,000 parts by weight based on 100 parts by weight of the polar solvent.

The reaction temperature is preferably from 0° to 180° C., and more preferably from 40° to 150° C. from the viewpoint of smoothly progressing the reaction and from the viewpoint of preventing a side reaction from taking place. The reaction time cannot be unconditionally determined, because the reaction time varies depending on the kinds of the 1,2-benzisothiazol-3-ones and the reaction temperature, and the reaction time is usually from 1 to 40 hours.

The method of isolating and purifying an intended 3-halo-1,2-benzisothiazole from a reaction mixture includes, for example, a method of vacuum distillation when the intended 3-halo-1,2-benzisothiazole is a liquid, a method of precipitation or extraction to recrystallize, when the intended product is a solid, and the like.

The 3-halo-1,2-benzisothiazole thus obtained is a compound represented by the above general formula (2).

In the above general formula (2), $R^1$ is the same group as the $R^1$ defined in the above general formula (1), and X is a halogen atom.

The halogen atom includes a fluorine atom, a chlorine atom, a bromine atom and the like.

Specific examples of the 3-halo-1,2-benzisothiazole represented by the above general formula (2) include 3-chloro-1,2-benzisothiazole, 3-chloro-7-methyl-1,2-benzisothiazole, 5-butyl-3-chloro-1,2-benzisothiazole, 3-chloro-6-methoxy-1,2-benzisothiazole, 3-chloro-6-methoxycarbonyl-1,2-benzisothiazole, 3-chloro-7-nitro-1,2-benzisothiazole, 3,6-dichloro-1,2-benzisothiazole, 3-bromo-1,2-benzisothiazole, 3-bromo-7-methyl-1,2-benzisothiazole, 5-butyl-3-bromo-1,2-benzisothiazole, 3-bromo-6-methoxy-1,2-benzisothiazole, 3-bromo-6-methoxycarbonyl-1,2-benzisothiazole, 3-bromo-7-nitro-1,2-benzisothiazole, 3,6-dibromo-1,2-benzisothiazole and the like.

EXAMPLES

The present invention will be specifically described hereinbelow by means of the Examples, without intending to limit the scope of the present invention thereto.

Example 1

A 1 L four-neck flask equipped with a stirrer, a thermometer and a condenser tube was charged with 75.6 g (0.5 mol) of 1,2-benzisothiazol-3-one, 54.8 g (0.75 mol) of N,N-dimethylformamide and 100.0 g of chlorobenzene. While stirring, 71.4 g (0.6 mol) of thionyl chloride was added dropwise thereto over 1 hour at 70° to 80° C., and the mixture was reacted at the same temperature for 8 hours. After terminating the reaction, the liquid reaction mixture was concentrated, and a crude product obtained was distillated under reduced pressure of 0.93 kPa at 128° C. to give 75.1 g (0.45 mol) of 3-chloro-1,2-benzisothiazole. The yield based on the 1,2-benzisothiazol-3-one was 90%.

Example 2

A 1 L four-neck flask equipped with a stirrer, a thermometer and a condenser tube was charged with 82.6 g (0.5 mol) of 7-methyl-1,2-benzisothiazol-3-one, 80.4 g (1.1 mol) of N,N-dimethylformamide and 200.0 g of toluene. While stirring, 83.3 g (0.7 mol) of thionyl chloride was added dropwise thereto at 70° to 80° C. over 1 hour, and the mixture was reacted at the same temperature for 3 hours. After terminating the reaction, the liquid reaction mixture was concentrated, and a crude product obtained was distilled under reduced pressure of 0.40 kPa at 110° C. to give 81.7 g (0.45 mol) of 3-chloro-7-methyl-1,2-benzisothiazole. The yield based on 7-methyl-1,2-benzisothiazol-3-one was 89%.

Example 3

A 1 L four-neck flask equipped with a stirrer, a thermometer and a condenser tube was charged with 90.6 g (0.5 mol) of 6-methoxy-1,2-benzisothiazol-3-one, 109.6 g (1.5 mol) of N,N-dimethylformamide and 150.0 g of chlorobenzene. While stirring, 89.2 g (0.75 mol) of thionyl chloride was added dropwise thereto at 80° to 90° C. over 1 hour, and the mixture was reacted at the same temperature for 5 hours. After terminating the reaction, the liquid reaction mixture was concentrated, and a crude product obtained was recrystallized from cyclohexane to give 86.9 g (0.44 mol) of 3-chloro-6-methoxy-1,2-benzisothiazole. The yield based on 6-methoxy-1,2-benzisothiazol-3-one was 87%.

Example 4

A 1 L four-neck flask equipped with a stirrer, a thermometer and a condenser tube was charged with 98.1 g (0.5 mol) of 7-nitro-1,2-benzisothiazol-3-one, 146.2 g (2 mol) of N,N-dimethylformamide and 500.0 g of chlorobenzene. While stirring, 119.0 g (1.0 mol) of thionyl chloride was added dropwise thereto at 80° to 90° C. over 1 hour, and the mixture was reacted at the same temperature for 3 hours. After terminating the reaction, the liquid reaction mixture was concentrated, and a crude product obtained was recrystallized from toluene to give 91.2 g (0.43 mol) of 3-chloro-7-nitro-1,2-benzisothiazole. The yield based on 7-nitro-1,2-benzisothiazol-3-one was 85%.

Comparative Example

The reaction was carried out in the same manner as in Example 4 except that 146.2 g of N,N-dimethylformamide in Example 4 was not used. However, the reaction did not progress, so that 3-chloro-7-nitro-1,2-benzisothiazole was not obtained.

Industrial Applicability

The 3-halo-1,2-benzisothiazole obtainable according to the method of the present invention is suitably used as production raw materials and the like for a medicament and the like.

The invention claimed is:

1. A method for producing a 3-halo-1,2-benzisothiazole represented by formula (2):

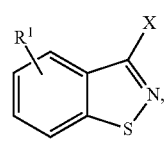

(2)

wherein R¹ is a hydrogen atom, an alkyl group having 1 to 4 carbon atoms, an alkoxy group having 1 to 4 carbon atoms, an alkoxycarbonyl group having 2 to 5 carbon atoms, a nitro group or a halogen atom, and X is a halogen atom, the method comprising reacting a 1,2-benzisothiazol-3-one represented by formula (1) with a thionyl halide in a polar solvent:

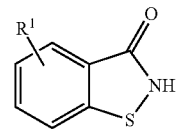

(1)

wherein R¹ is as defined in formula (2), and
wherein the amount of the polar solvent is 1 to 6 mol based on 1 mol of 1,2-benzisothiazol-3-one.

2. The method according to claim 1, wherein the thionyl halide is thionyl chloride.

3. The method according to claim 1, wherein the thionyl halide is used in an amount of from 0.8 to 5 mol based on 1 mol of 1,2-benzisothiazol-3-one.

4. The method according to claim 1, wherein the polar solvent is N,N-dimethylformamide.

5. The method according to claim 1, wherein X is F.

6. The method according to claim 1, wherein X is Cl.

7. The method according to claim 1, wherein X is Br.

8. The method according to claim 1, wherein the 1,2-benzisothiazol-3-one represented by formula (1) is 1,2-benzisothiazol-3-one, 7-methyl-1,2-benzisothiazol-3-one, 5-butyl-1,2-benzisothiazol-3-one, 6-methoxy-1,2-benzisothiazol-3-one, 6-methoxycarbonyl-1,2-benzisothiazol-3-one, 7-nitro-1,2-benzisothiazol-3-one, or 6-chloro-1,2-benzisothiazol-3-one.

9. The method according to claim 1, wherein the polar solvent is N,N-diethylformamide, N,N-dibutylformamide, sulfolane, or pyridine.

10. The method according to claim 1, wherein the amount of the polar solvent is 1.5 to 5.5 mol based on 1 mol of 1,2-benzisothiazol-3-one.

11. The method according to claim 1, wherein the amount of the polar solvent is 2.2 to 5 mol based on 1 mol of 1,2-benzisothiazol-3-one.

12. The method according to claim 1, wherein the reaction also contains at least one inert solvent selected from the group consisting of hydrocarbons, halogenated hydrocarbons, and aromatic hydrocarbons.

13. The method according to claim 1, wherein the inert solvent comprises toluene or chlorobenzene.

14. The method according to claim 1, wherein the 3-halo-1,2-benzisothiazole represented by formula (2) is 3-chloro-1,2-benzisothiazole, 3-chloro-7-methyl-1,2-benzisothiazole, 5-butyl-3-chloro-1,2-benzisothiazole, 3-chloro-6-methoxy-1,2-benzisothiazole, 3-chloro-6-methoxycarbonyl-1,2-benzisothiazole, 3-chloro-7-nitro-1,2-benzisothiazole, 3,6-dichloro-1,2-benzisothiazole, 3-bromo-1,2-benzisothiazole, 3-bromo-7-methyl-1,2-benzisothiazole, 5-butyl-3-bromo-1,2-benzisothiazole, 3-bromo-6-methoxy-1,2-benzisothiazole, 3-bromo-6-methoxycarbonyl-1,2-benzisothiazole, 3-bromo-7-nitro-1,2-benzisothiazole, or 3,6-dibromo-1,2-benzisothiazole.

* * * * *